US008781599B2

(12) United States Patent
Henshaw et al.

(10) Patent No.: US 8,781,599 B2
(45) Date of Patent: Jul. 15, 2014

(54) FLEXIBLE PROTECTED LEAD

(75) Inventors: Scott Henshaw, Macquarie University (AU); Roger Leigh, Macquarie University (AU); Krzysztof Tarrell, Macquarie University (AU); Grahame Walling, Macquarie University (AU)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 13/208,730

(22) Filed: Aug. 12, 2011

(65) Prior Publication Data
US 2013/0041448 A1 Feb. 14, 2013

(51) Int. Cl.
*A61N 1/05* (2006.01)

(52) U.S. Cl.
USPC ............................................. 607/115; 607/137

(58) Field of Classification Search
USPC ........................................ 607/115, 116, 137
See application file for complete search history.

(56) References Cited

U.S. PATENT DOCUMENTS

| 5,545,219 | A | 8/1996 | Kuzma |
| 5,674,272 | A | 10/1997 | Bush et al. |
| 5,674,273 | A | 10/1997 | Helland |
| 5,876,430 | A * | 3/1999 | Shoberg et al. ............... 607/122 |
| 7,519,432 | B2 * | 4/2009 | Bolea et al. .................... 607/116 |
| 7,761,170 | B2 * | 7/2010 | Kaplan et al. .................. 607/116 |
| 7,996,092 | B2 * | 8/2011 | Mrva et al. ..................... 607/118 |
| 8,244,372 | B1 * | 8/2012 | Zhulati et al. ................. 607/116 |
| 2003/0069613 | A1 | 4/2003 | Kuzma et al. |
| 2004/0088033 | A1 * | 5/2004 | Smits et al. ................... 607/122 |
| 2006/0206185 | A1 | 9/2006 | Schuller |
| 2007/0071252 | A1 | 3/2007 | Burger et al. |
| 2007/0225784 | A1 * | 9/2007 | Bly et al. ....................... 607/116 |
| 2008/0082141 | A1 | 4/2008 | Risi |
| 2009/0023976 | A1 | 1/2009 | Cho et al. |
| 2010/0204768 | A1 | 8/2010 | Jolly et al. |
| 2010/0305676 | A1 | 12/2010 | Dadd et al. |
| 2011/0160820 | A1 * | 6/2011 | Jackson et al. ................ 607/116 |

FOREIGN PATENT DOCUMENTS

| EP | 1385355 A1 | 1/2004 |
| WO | 2010033369 | 3/2010 |

OTHER PUBLICATIONS

International Preliminary Report on Patentability for PCT/IB2012/053589 issued on Feb. 18, 2014.

* cited by examiner

*Primary Examiner* — Brian T Gedeon
(74) *Attorney, Agent, or Firm* — McDonnell Boehnen Hulbert & Berghoff LLP

(57) ABSTRACT

Designs for an implantable lead are disclosed. In one embodiment, the lead includes at least one conductive pathway and a protective element surrounding at least a portion of the at least one conductive pathway. A stiffness of the protective element varies along a length of the protective element. The stiffness may be varied by varying a material composition of the protective element. Alternately, the protective element may be one or two helically-wound wires, and the stiffness may be varied by varying a pitch of one or both helically-wound wires. Alternately, the protective element may be a perforated tube and the stiffness may be varied by varying a ratio of openings to tube in the perforated tube. Alternately, the protective element may be a patterned mesh and the stiffness may be varied by varying a pattern of the patterned mesh. The implantable lead may be used in a cochlear implant.

27 Claims, 12 Drawing Sheets

FLEXIBLE PROTECTED LEAD

BACKGROUND

Cochlear implants may provide a person having sensorineural hearing loss with the ability to perceive sound by stimulating the person's auditory nerve via an array (or other configuration) of electrodes implanted in the person's cochlea. Typically, the cochlear implant functions to detect sound waves, convert the sound waves into a series of electrical stimulation signals, and deliver the stimulation signals to the cochlear implant recipient's auditory nerve via the array of electrodes. Stimulating the auditory nerve in this manner may enable the cochlear implant recipient's brain to perceive a hearing sensation that is similar to the natural hearing sensation delivered to a properly functioning auditory nerve.

Cochlear implant systems typically consist of two key components, namely an external component, such as a BTE (behind the ear) component, and an internal component. The external and internal components operate together to deliver the hearing sensation to the cochlear implant recipient.

The internal component of a cochlear implant system typically includes one or more leads configured to connect the internal component of the cochlear implant to various modules including, for example, an electrode array, a reference electrode, connectors, batteries, and systems, such as, for example, a Direct Acoustic Cochlear Stimulation (DACS) system. Further, some cochlear implant systems are designed to be fully-implantable cochlear implant systems in which one or both of a microphone and a speech processor are implanted in the cochlear implant recipient along with the internal component. Accordingly, upgradeable and fully-implantable cochlear implant systems may include one or more leads configured to connect the internal component of the cochlear implant system to a microphone, a speech processor, and/or other modules.

In some cases, there may be a need to access one or more leads on an internal component after the internal component has been implanted in the cochlear implant recipient. For example, a battery connected to a lead of the internal component may need to be replaced. As another example, in an upgradeable cochlear implant system, a microphone or speech processor may need to be implanted and connected to one or more leads in order to upgrade the cochlear implant system to a fully-implantable cochlear implant system. Other examples are possible as well. In order to access the leads, one or more surgical procedures may be performed.

During such surgical procedures, the leads of the internal component may be at risk. In particular, surgical instruments (e.g., scalpels, burrs, or forceps) used during the surgical process may nick, slice, or otherwise damage the lead.

SUMMARY

The present application discloses an implantable lead with a protective element that may protect the lead from one or more of the risks described above. The implantable lead comprises at least one conductive pathway and a protective element surrounding at least a portion of the at least one conductive pathway. A stiffness of the protective element varies along a length of the protective element. In some embodiments, an overall stiffness of the protective element may be reduced, such that the protective element allows for protection against damage while remaining malleable.

In one example, the protective element comprises a first helically-wound wire, and the stiffness varying along the length of the protective element involves a pitch of the first helically-wound wire varying along a length of the first helically-wound wire. The first helically-wound wire may include a first plurality of turns at an angle between about 15° and 75° relative to a length of the implantable lead.

In another example, the protective element further comprises a second helically-wound wire that at least partially surrounds the first helically-wound wire. The second helically-wound wire may include a plurality of turns at an angle between about 15° and 75° relative to the length of the implantable lead and non-parallel to the first plurality of turns. The stiffness varying along the length of the protective element may involve a pitch of the second helically-wound wire varying along the length of the second helically-wound wire.

In yet another example, the protective element comprises a perforated tube, and the stiffness varying along the length of the protective element involves a ratio of cuts to tube in the perforated tube varying along a length of the perforated tube.

In still another example, the protective element comprises a patterned mesh, and the stiffness varying along the length of the protective element involves a pattern of the patterned mesh varying along a length of the patterned mesh.

In yet another example, the stiffness varying along the length of the protective element involves a material composition of the protective element varying along the length of the protective element.

In still another example, the stiffness varying along the length of the protective element involves the stiffness reducing along the length of the protective element.

An implantable device is also disclosed. The implantable device includes a lead, and the lead includes a connector, at least one conductive pathway, and a protective element surrounding at least a portion of the at least one conductive pathway. A stiffness of the protective element varies along a length of the protective element.

In one example, the protective element extends from the connector along a length of the lead. The stiffness of the protective element varying along a length of the protective element involves the stiffness being greatest at the connector and reducing along the length of the lead away from the connector.

In another example, the protective element extends along substantially the entire length of the lead.

In yet another example, the protective element comprises a first helically-wound wire and a second helically-wound wire surrounding the first helically-wound wire. The first helically-wound wire may comprise a plurality of turns, each turn being at an angle between about 15° and 75° relative to the length of the lead, and the second helically-wound wire may comprise a second plurality of turns, each turn being at an angle between about 15° and 75° relative to the length of the lead and non-parallel to the first plurality of turns. A stiffness of the protective element varying along a length of the protective element may involve varying a pitch of the first helically-wound wire along the length of the first helically-wound wire or varying a pitch of the second helically-wound wire along the length of the second helically-wound wire, for example.

A cochlear implant is also disclosed. The cochlear implant includes a stimulator configured to generate a stimulation current, a first lead configured to conduct the stimulation current between the stimulator and at least one stimulation site, and a second lead configured to connect the stimulator to a separate module. The second lead includes a connector, at least one conductive pathway, and a protective element surrounding at least a portion of the at least one conductive pathway. A stiffness of the protective element varies along a length of the protective element.

In one example, the protective element extends from the connector along a length of the second lead. The stiffness of the protective element varying along a length of the protective element involves the stiffness being greatest at the connector and reducing along the length of the second lead away from the connector.

In another example, the protective element comprises a first helically-wound wire and a second helically-wound wire surrounding the first helically-wound wire. The first helically-wound wire may comprise a plurality of turns, each turn being at an angle between about 15° and 75° relative to the length of the second lead, and the second helically-wound wire may comprise a second plurality of turns, each turn being at an angle between about 15° and 75° relative to the length of the second lead and non-parallel to the first plurality of turns. A stiffness of the protective element varying along a length of the protective element may involve varying a pitch of the first helically-wound wire along the length of the first helically-wound wire or varying a pitch of the second helically-wound wire, for example.

In yet another example, the first lead additionally comprises a protective element.

DETAILED DESCRIPTION

The following detailed description describes various features and functions of the disclosed designs with reference to the accompanying figures. In the figures, similar symbols typically identify similar components, unless context dictates otherwise. The illustrative embodiments described herein are not meant to be limiting. Certain aspects of the disclosed designs can be arranged and combined in a wide variety of different configurations, all of which are contemplated herein.

1. Cochlear Implant Overview

Figure 1:
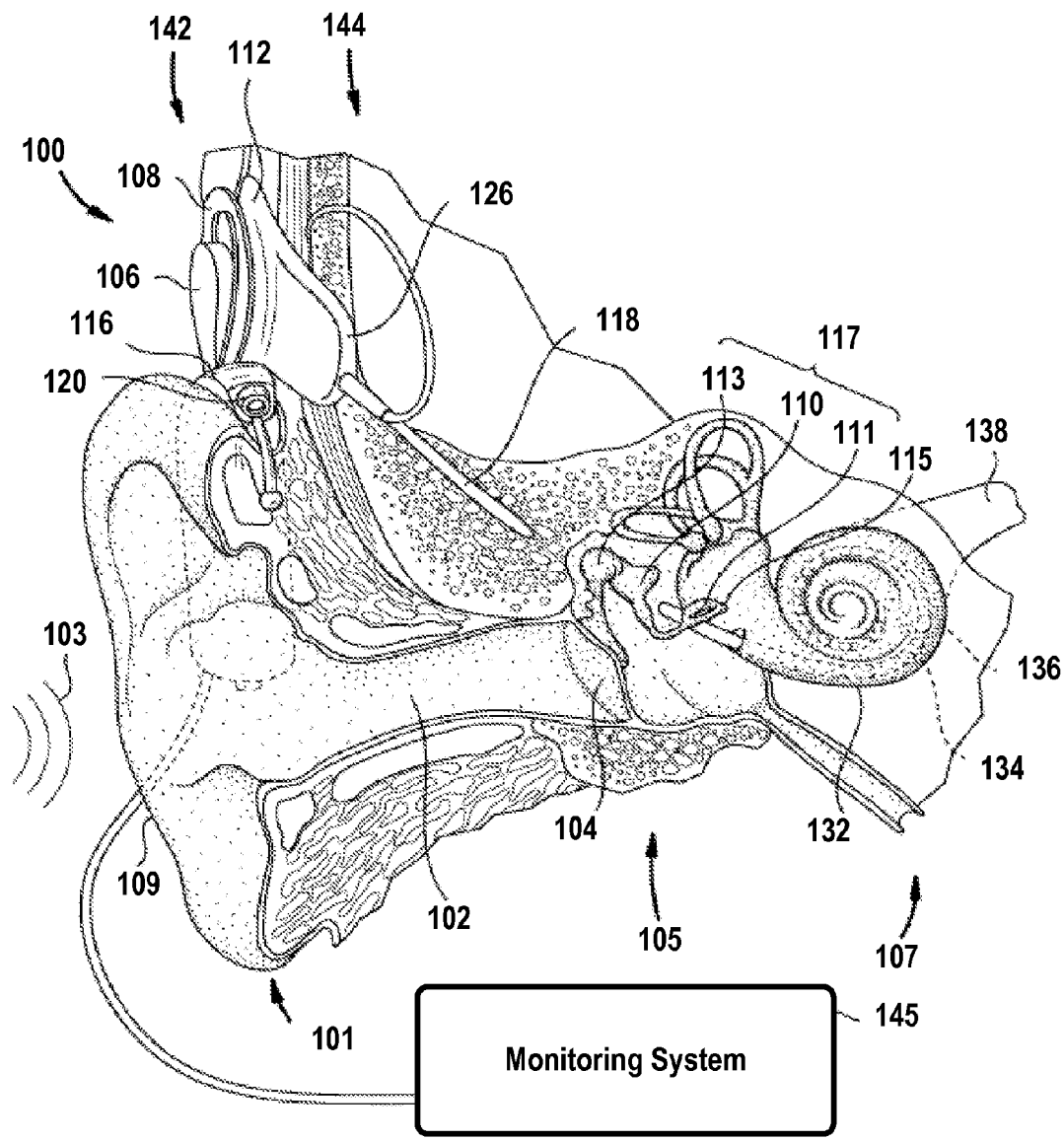
FIG. 1 shows an example of a typical cochlear implant that may be implanted into a cochlear implant recipient.

FIG. 1 shows an example of a typical cochlear implant that may be implanted into an implant recipient. As shown, the cochlear implant 100 may include an external component 142 that is directly or indirectly attached to the body of the recipient, and an internal component 144 that is implanted in the recipient.

The external component 142 may include a sound processor 116 and an external transmitter unit 106. The sound processor 116 may include a digital signal processor (DSP), a power source to power the cochlear implant 100, and a sound transducer 120. The sound transducer 120 may be configured to detect sound and generate an audio signal, such as an analog audio signal, representative of the detected sound. In the example embodiment shown in FIG. 1, the sound transducer 120 is a microphone. In alternative embodiments, the sound transducer 120 may comprise, for example, more than one microphone, one or more telecoil induction pickup coils, or other devices now or later developed that may detect sound and generate stimulation signals representative of detected sound. In some embodiments, the sound transducer 120 may not be integrated into the sound processor 116, but rather could be a separate part of the external component 142.

The external transmitter unit 106 may include an external transmitter coil 108 along with associated circuitry to drive the coil. The external transmitter unit 106 may also preferably include a magnet (not shown) secured directly or indirectly to the external transmitter coil 108.

The sound processor 116 may be configured to process the output of the microphone 120. The sound processor 116 may be configured to generate coded signals, which can be provided to the external transmitter unit 106 via a cable (not shown).

The internal component 144 may include an internal receiver unit 112, a stimulator 126, and a first lead 118. The internal receiver unit 112 and the stimulator 126 may be hermetically sealed within a bio-compatible housing.

The internal receiver unit 112 may include an internal receiver coil (not shown) along with the associated circuitry. The implanted internal receiver unit 112 may be positioned in a recess of the temporal bone adjacent to the outer ear 101 of the recipient, as shown in FIG. 1. The external transmitter coil 108 may be held in place and aligned with the implanted internal receiver coil via the above-referenced magnets. As set forth earlier, the external transmitter coil 108 may be configured to transmit the coded signals from the sound processor 116 and power from the power source to the internal coil via a radio frequency (RF) link.

The first lead 118 may be designed to extend from the stimulator 126 to the cochlea 132 and to terminate in an array 134 of electrode contacts 136. Signals generated by the stimulator 126 are applied by the electrode contacts 136 to the cochlea 132, thereby stimulating the auditory nerve 138.

Figure 2A:
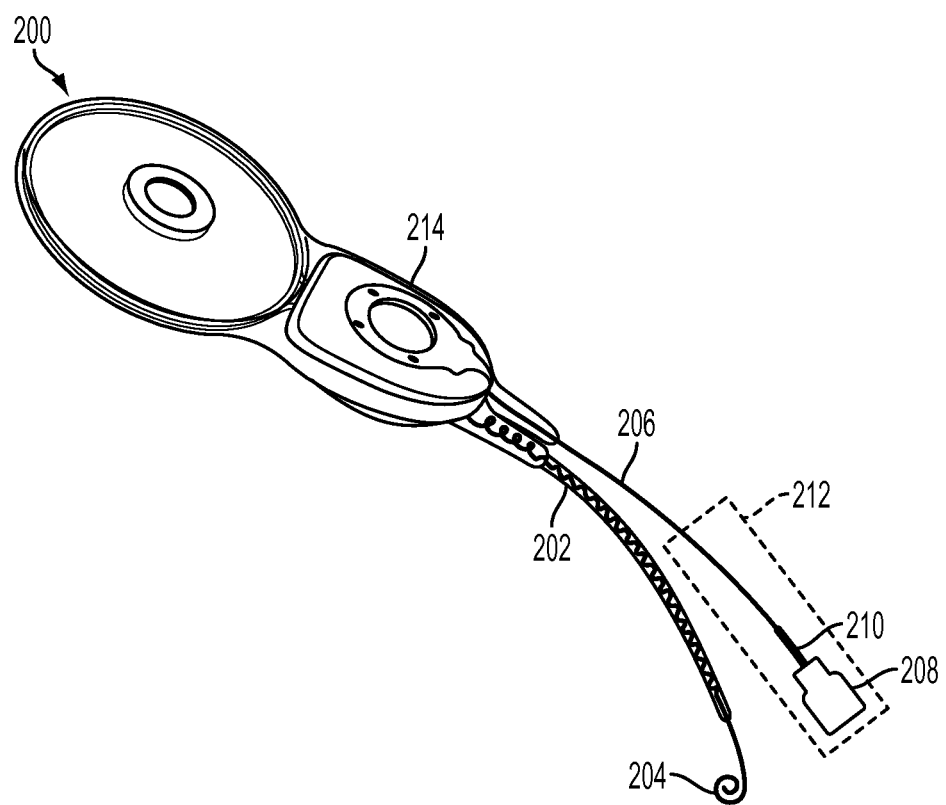
FIGS. 2A-2B show an internal component of an example cochlear implant including a protective element (FIG. 2A) and a lead from the example cochlear implant (FIG. 2B)

FIG. 2A shows an example internal component of a cochlear implant system, in accordance with an embodiment. As shown, the internal component 200 includes leads 202, 206. The internal component 200 further includes a stimulator 214 configured to generate a stimulation current, as described above.

As shown, the internal component 200 includes a first lead 202 configured to conduct the stimulation current between the stimulator 214 and a plurality (e.g., an array) of electrode contacts 204 that may be placed in a cochlea.

Further, the internal component 200 includes a second lead 206 configured to connect the internal component 200 to a separate module. To this end, the second lead 206 includes a connector 208 that is connectable to the separate module. The separate module may be, for example, a microphone or other sound transducer, a power source, and/or a speech processor. Other separate modules are possible as well.

As noted above, each of the first lead 204 and the second lead 206 may be at risk of damage by surgical instruments during surgical procedures. Moreover, the leads 202, 206 may pose a particular challenge if, over time, bony growth and/or tissue has formed around the leads 202, 206. For this reason, it may be desirable to include on at least the second lead 206 a protective element that at least partially surrounds the second lead 206, as shown in FIG. 2B.

Figure 2B:
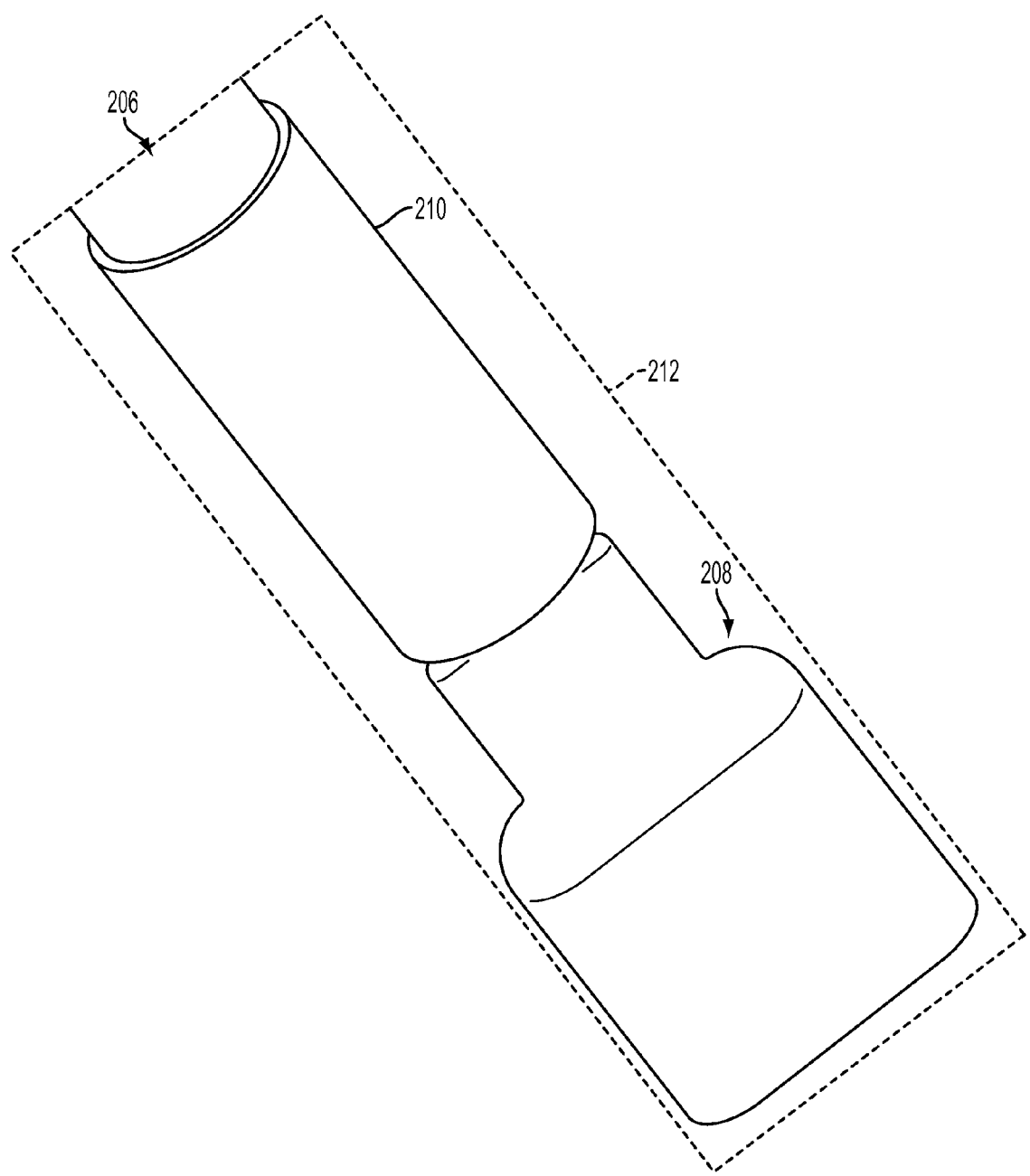

FIG. 2B is a more detailed view of a portion 212 of the second lead 206 and the connector 208 shown in FIG. 2A. As can be seen in FIG. 2B, the second lead 206 includes a protective element 210 that surrounds at least a portion of the second lead 206.

Generally, inclusion of a protective element on a lead may have negative effects on the performance of the lead. For example, the protective element may result in a concentration of stress at one or more points along the lead that may be susceptible to breakage. As another example, the protective element may increase a stiffness or reduce the malleability of the lead, making the lead difficult to position during implantation of the cochlear implant. There may be other negative effects as well.

In order to avoid such negative effects, in the protective element 210 a stiffness of the protective element 210 may be varied along a length of the protective element 210. By varying the stiffness along the length of the protective element 210, some or all of the negative effects described above may be avoided. For example, the stiffness of the protective element 210 may be gradually varied along the protective element so that concentrations of stress are avoided. As another example, the stiffness of the protective element 210 may be reduced in particular portions of the protective element to aid in positioning the second lead 206 during implantation of the cochlear implant. As still another example, the stiffness of the protective element 210 may be reduced overall to allow for protection against damage of the lead while remaining malleable. Other examples are possible as well.

Such variation in the stiffness of the protective element 210 may take many forms. For example, the stiffness of the protective element 210 may be reduced towards one or both ends of the protective element 210 so as to avoid concentrations of stress at the transitions between the protective element 210 and the second lead 206. As another example, the stiffness of the protective element 202 may be greatest near the connector 208 and may reduce along the length of the second lead 206 away from the connector 208. Other examples are possible as well.

As shown, the protective element 210 extends from the connector 208 along a length of the second lead 206. However, the protective element 210 may extend along any length of the second lead 206 and may extend between any two points along the length of the second lead 206. For example, the protective element 210 may extend along substantially the entire length of the second lead 206. As another example, the protective element 210 may begin within and/or may be integrated into the connector 208 and may extend along some or all of the lead 206 away from the connector 208. Other examples are possible as well.

In some embodiments, the second lead 206 may include one or more additional protective elements. The protective elements may be, for example, overlapping, at discrete locations along the lead, or adjacent to one another. Other examples are possible as well. In other embodiments, the first lead 202 may similarly include one or more protective elements.

2. Flexible Protected Lead

Variation in the stiffness of the protective element may be achieved in various ways, depending on the form of the protective element. The following embodiments illustrate several example forms of protective elements and ways of varying the stiffness of the protective elements. These may be implemented separately or in combination with one another.

a. Protective Element with Varying Material Concentration

Figure 3A:
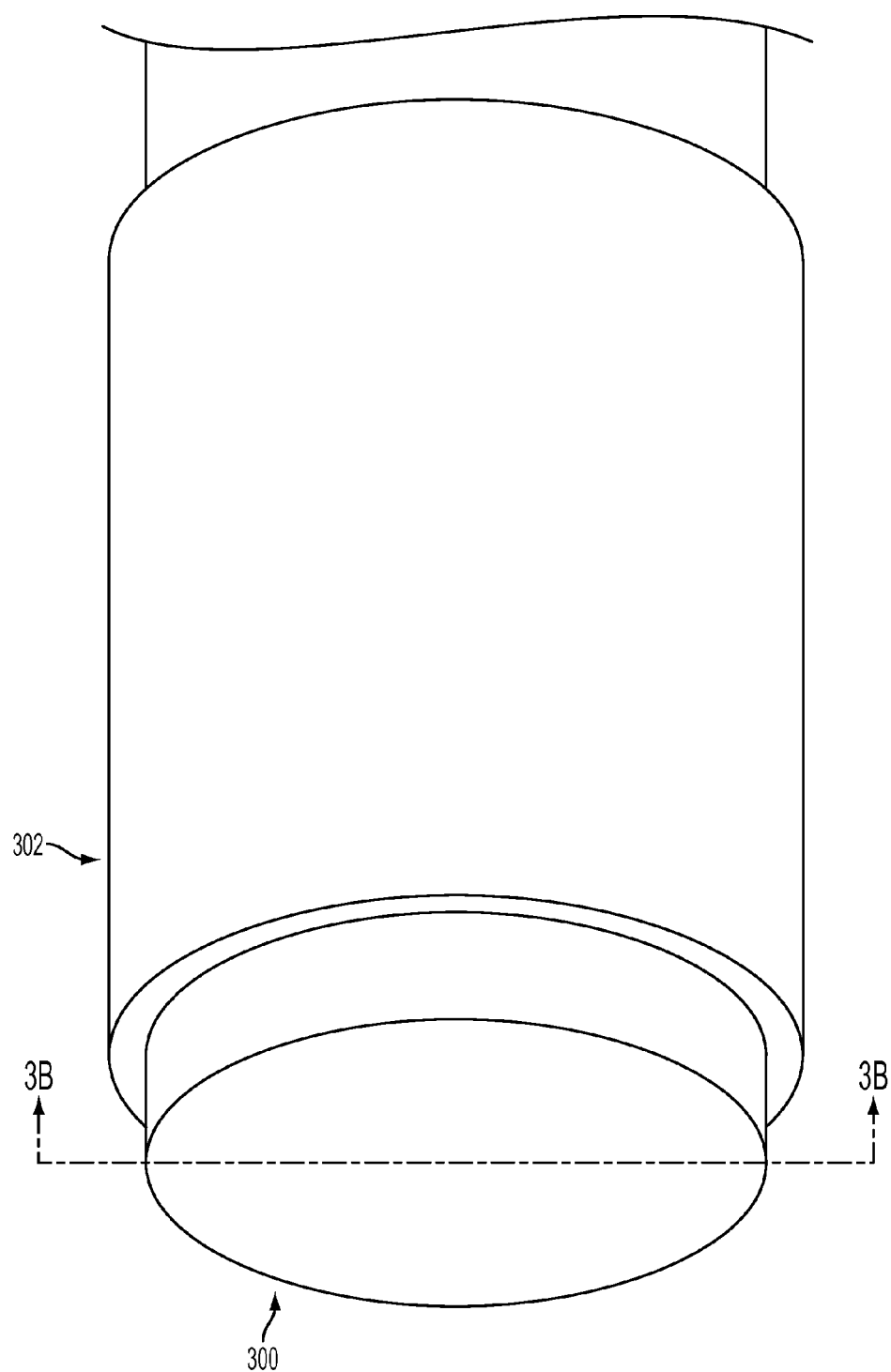
FIGS. 3A-B show an overview (FIG. 3A) and a cross-sectional view (FIG. 3B) of an example lead including a flexible protective element, in accordance with an embodiment.
Figure 3B:
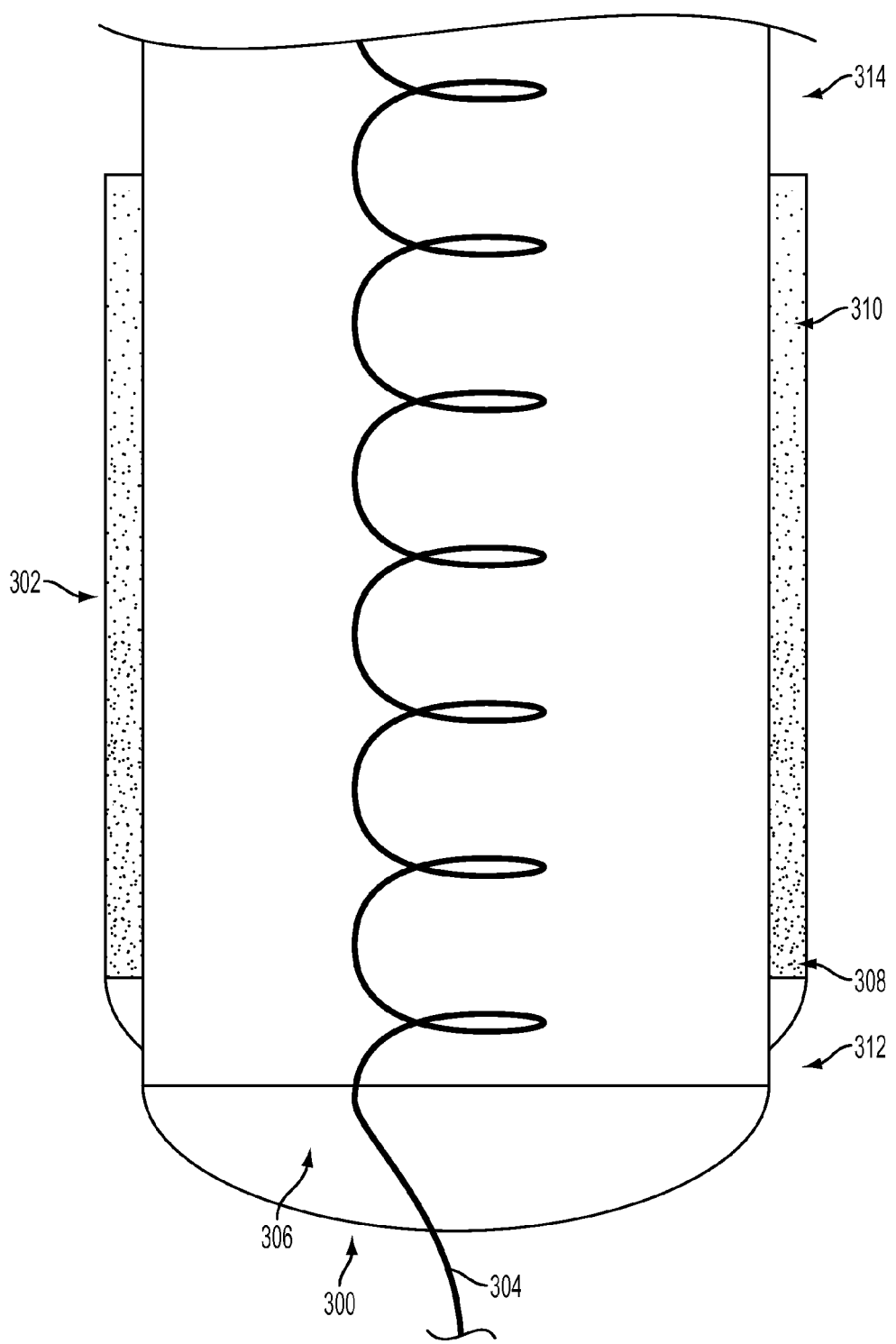

FIGS. 3A-B show an overview (FIG. 3A) and a cross-sectional view (FIG. 3B) of an example lead 300 including a flexible protective element 302, in accordance with an embodiment. As shown, the lead 300 includes a protective element 302 that surrounds at least a portion of the second lead 300. The protective element 302 may be formed of a number of materials and material compositions including, for example, a metal, a metal alloy, or a polymer. In one example, the protective element 302 may be formed of a bio-compatible material. Other examples are possible as well.

The cross-sectional view shown in FIG. 3B is a cross-section of the lead 300 cut along the line 3B-3B from FIG. 3A. As shown, the lead 300 includes at least one conductive pathway 304 surrounded by a material 306. The conductive pathway 304 may, in some embodiments, comprise multiple conductive pathways. Further, the conductive pathway 304 may take a variety of paths through the lead, including, for example undulating, helically wound, straight, randomly formed, and/or combinations thereof. The material 306 may be, for example, a silicone rubber and may be formed by, for example, moulding so as to fully encase the conductive pathway 304. The material 306 may take other forms as well.

As shown, the protective element 302 is located on an exterior surface of the lead 300. In some embodiments, however, the protective element 302 may instead be encased within the lead 300. For example, the material 306 may surround the protective element 302. Alternatively, an additional layer of material, such as silicone rubber, polyurethane or the like, may surround all or a portion of the protective element.

As noted above, a stiffness of the protective element 302 may be varied along a length of the protective element 302. In the embodiment shown in FIG. 3B, the varied stiffness of the protective element 302 is achieved by varying a material composition of the protective element 302 along the length of the protective element 302. As shown, a first material composition 308 at one end 312 of the protective element 302 differs from a second material composition 310 at the other end 314 of the protective element 302. In one example, the first material composition 308 may have an increased flexibility and/or decreased resistance to separation or penetration from pressure (e.g., cutting, puncturing or other damage) as compared with the second material composition 310 as a result of, for example, an increased concentration of a particular material in the first material composition 308 as compared with the second material composition 310. Other examples are possible as well.

As a result of the variation from the first material composition 308 to the second material composition 310, a stiffness of the protective element 302 may vary from one end 312 of the protective element 302 to the other end 314.

While only two material compositions are labeled, it is to be understood that the material composition may vary along the entire length of the protective element 302. In one example, the material composition may be varied such that a stiffness of the protective element 302 increases from one end of the protective element 302 to the other. In another example, the material composition may be varied such that a stiffness of the protective element 302 decreases from one end of the protective element 302 to the other. In particular, the material composition may be varied such that a stiffness of the lead 300 is highest near the connector and decreases along the lead 300 towards the internal component. In still another example, the material composition may be varied such that a stiffness of the protective element 302 is greatest towards the middle or other point along the length of the protective element 302 and reduces towards the ends of the protective element 302. In yet another example, the material composition may be varied such that a stiffness of the protective element 302 both increases and decreases one or more times from one end of the protective element 302 to the other. In still another example, the material composition may be varied along some portions of the protective element 302 and may remain constant along other portions of the protective element 302. Other examples are possible as well.

b. Helically-Wound Wire Protective Element

Figure 4A:
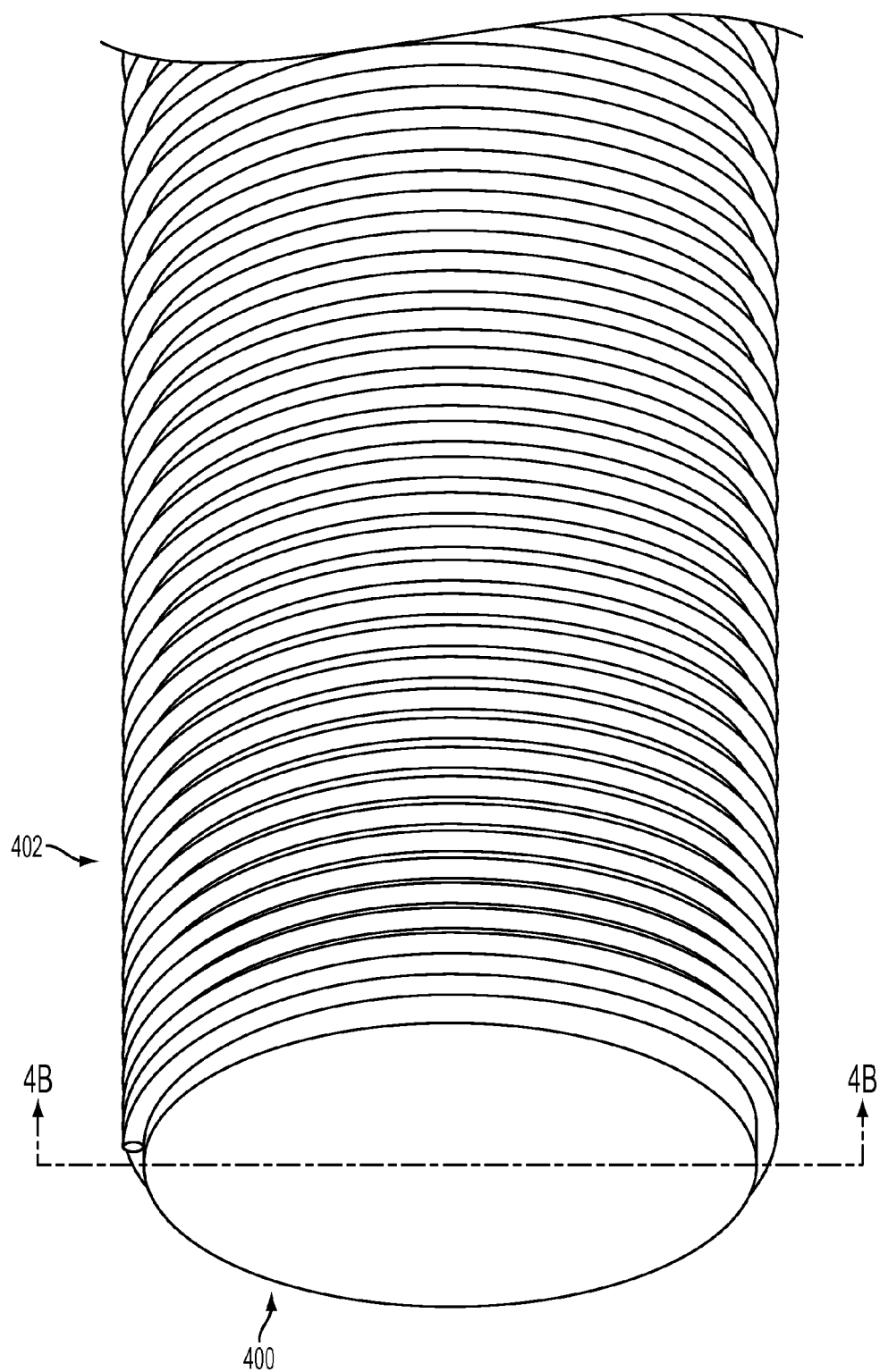
FIGS. 4A-B show an overview (FIG. 4A) and a cross-sectional view (FIG. 4B) of an example lead including a protective element comprising a helically-wound wire, in accordance with an embodiment.
Figure 4B:
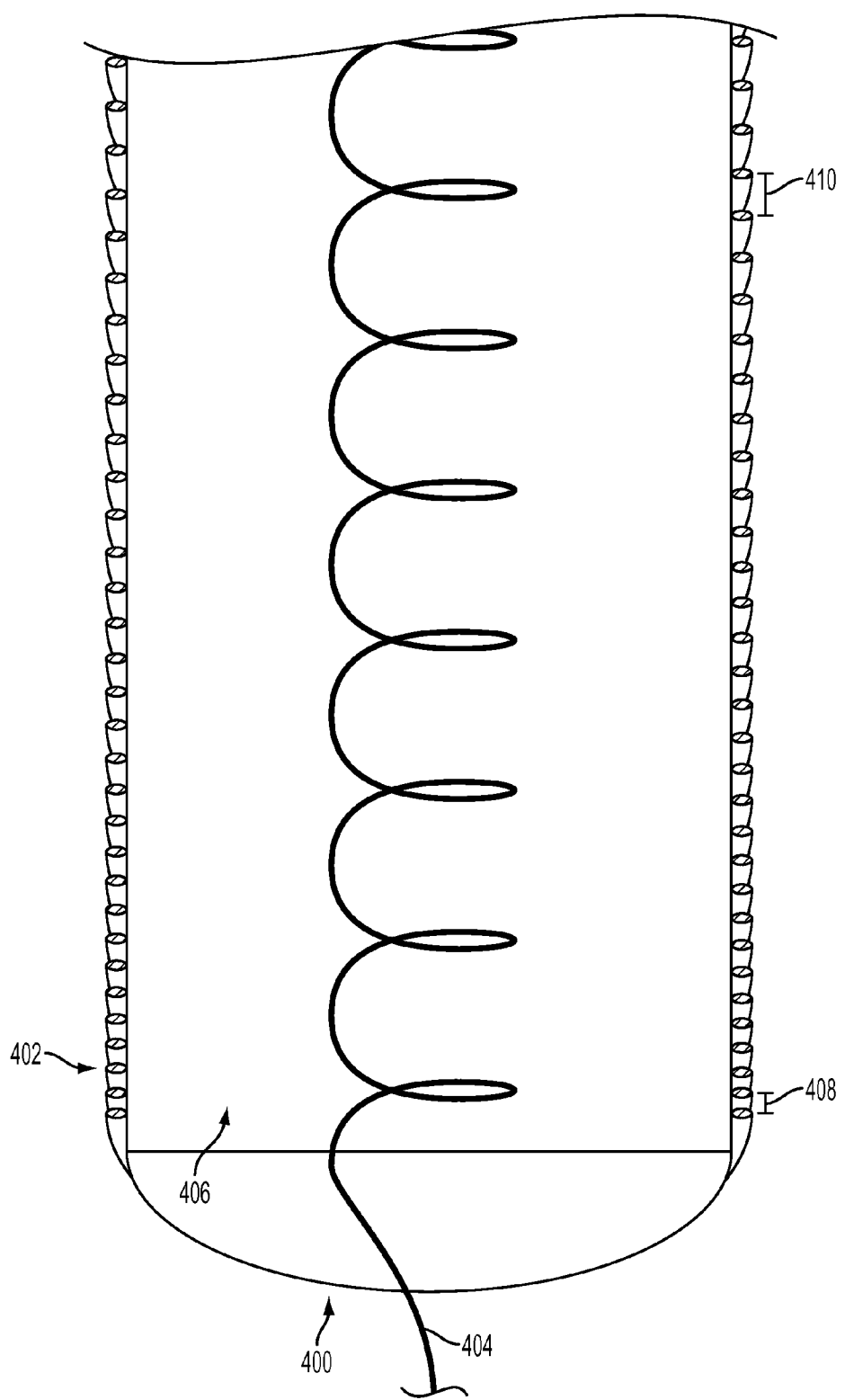

FIGS. 4A-B show an overview (FIG. 4A) and a cross-sectional view (FIG. 4B) of an example lead 400 including a protective element comprising a helically-wound wire 402, in accordance with an embodiment. As shown (in simplified fashion), the lead 400 includes a helically-wound wire 402 that serves as a protective element and surrounds at least a portion of the second lead 400. The helically-wound wire 402 may be formed of a number of materials and material compositions including, for example, a metal or a metal alloy. In one example, the helically-wound wire 402 may be formed of a bio-compatible material, such as titanium, platinum, or stainless steel. Other materials are possible as well. Further, the helically-wound wire 402 may have a variety of cross-sectional shapes including, for example, a round, square, or oblong and/or ribbon-like shape. Other cross-sections are possible as well. Still further, the wire of the helically-wound wire 402 may have a variety of diameters, such as a diameter in the range of 25 µm to 300 µm, or in some embodiments in the range of 50 µm to 100 µm. Other diameters are possible as well.

The helically-wound wire 402 includes a plurality of turns at an angle relative to the length of the lead 400. The angle may be between, for example, about 0° and 90° in either direction, relative to the length of the lead. Other examples are possible as well. In this manner, the helically-wound wire 402 may form a sort of canted spring. In some embodiments, the angle may be the same for each turn in the plurality of turns. In other embodiments, the angle may vary from turn to turn so as to, for example, create a curve or bend in the lead 400. The helically-wound wire 402 may be wound clockwise and/or counterclockwise. Other examples are possible as well.

The cross-sectional view shown in FIG. 4B is a cross-section of the lead 400 cut along the line 4B-4B from FIG. 4A. As shown, the lead 400 includes at least one conductive pathway 404 surrounded by a material 406. Each of the conductive pathway 404 and the material 406 may take any of the forms described above in connection with FIGS. 3A-B.

As shown, the helically-wound wire 402 surrounds the lead 400. In some embodiments, however, the helically-wound wire 402 may instead be encased within the lead 400. For example, the material 406 may surround the helically-wound wire 402. Alternatively, an additional layer of material, such as silicone rubber, polyurethane or the like, may surround all or a portion of the helically-wound wire 402. Other configurations are possible as well, including those involving additional conductive pathways 404 and/or materials 406.

As noted above, a stiffness of the protective element (embodied in this example by the arrangement of the helically-wound wire 402) may be varied along a length of the protective element. In the embodiment shown in FIG. 4B, the varied stiffness is achieved by varying a distance between turns, or a "pitch", of the helically-wound wire 402 along the length of the lead 400 (and, accordingly, along the length of the helically-wound wire 402). As shown, a first pitch 408 at a first location along the helically-wound wire 402 differs from a second pitch 410 at a second location along the helically-wound wire 402. As a result of the pitch variation between the first pitch 408 and the second pitch 410, a stiffness of the lead 400 may vary from one part of the helically-wound wire 402 to another part. In particular, as shown, because the first pitch 408 is smaller than the second pitch 410, the lead 400 may be stiffer near the first pitch 408 than near the second pitch 410.

While only two pitches are labeled, it is to be understood that more than two pitches are possible and the pitch of the helically-wound wire 402 may vary at some or all points along the length of the helically-wound wire 402. In one example, the pitch may be varied such that a stiffness of the lead 400 increases from one end of the helically-wound wire 402 to the other (i.e., from a first part of the lead 400 to a second part). In another example, the pitch may be varied such that a stiffness of the lead 400 decreases from one end of the helically-wound wire 402 to the other. In particular, the pitch may be varied such that a stiffness of the lead 400 is highest near the connector and decreases along the lead 400 towards the internal component. In still another example, the pitch may be varied such that a stiffness of the lead 400 is greatest towards the middle or other point along the length of the helically-wound wire 402 and reduces towards the ends of the helically-wound wire 402. In yet another example, the pitch may be varied such that a stiffness of the lead 400 both increases and decreases one or more times from one end of the helically-wound wire 402 to the other. In still another example, the pitch may be varied along some portions of the helically-wound wire 402 and may remain constant along other portions of the helically-wound wire 402. Other examples are possible as well.

c. First and Second Helically-Wound Wires Protective Element

Figure 5A:
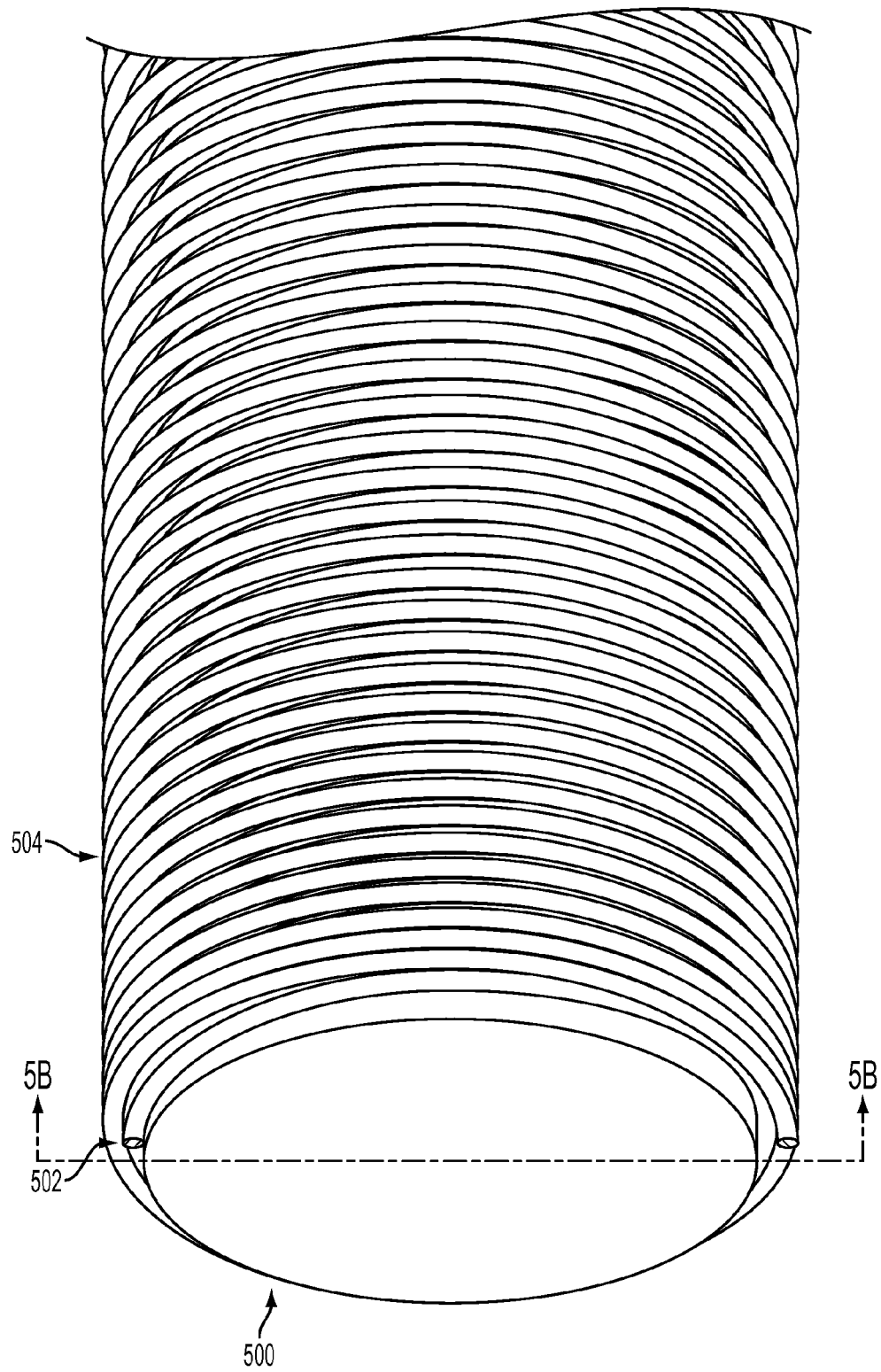
FIGS. 5A-B show an overview (FIG. 5A) and a cross-sectional view (FIG. 5B) of an example lead including a protective element comprising two helically-wound wires, in accordance with an embodiment.
Figure 5B:
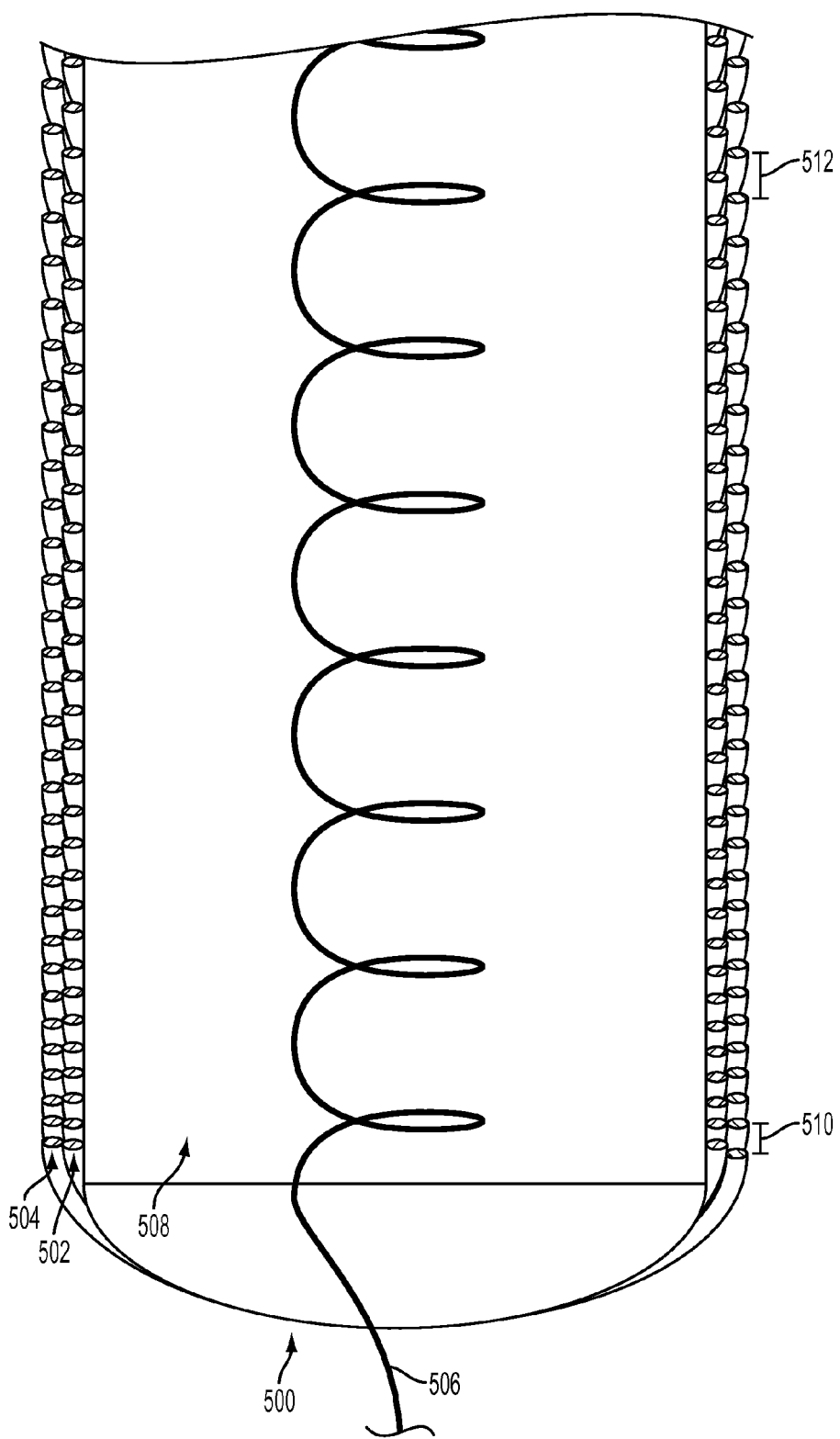

FIGS. 5A-B show an overview (FIG. 5A) and a cross-sectional view (FIG. 5B) of an example lead 500 including a protective element comprising two helically-wound wires 502, 504, in accordance with an embodiment. As shown, the lead 500 includes a first helically-wound wire 502 and a second helically-wound wire 504 that together serve as a protective element. In the example shown, the first helically-wound wire 502 surrounds the lead 500, while the second helically-wound wire 504 overlays the first helically-wound wire 502. To this end, the second helically-wound wire 504 may have an internal diameter that is larger than an external diameter of the first helically-wound wire 502. In another example, a portion of the first helically-wound wire 502 may be wound back onto itself to form the second helically-wound wire 504, such that the first helically-wound wire 502 and the second helically-wound wire 504 are formed of a single wire. Other examples are possible as well.

Each of the first helically-wound wire 502 and the second helically-wound wire 504 may be formed of a number of materials and material compositions including, for example, a metal or a metal alloy. In one example, one or both of the first helically-wound wire 502 and the second helically-wound wire 504 may comprise a bio-compatible material, such as titanium, platinum, or stainless steel. Other materials are possible as well. The first helically-wound wire 502 and the second helically-wound wire 504 may be made of the same or of differing materials. Further, each of the first helically-wound wire 502 and the second helically-wound wire 504 may have a variety of cross-sectional shapes including, for example, a round, square, or oblong and/or ribbon-like shape. Other cross-sections are possible as well. The first helically-wound wire 502 and the second helically-wound wire 504 may have the same or differing cross-sectional shapes. Still further, the wire of each of the first helically-wound wire 502 and the wire of the second helically-wound wire 504 may have a variety of diameters, such as a diameter in the range of 25 µm to 300 µm, or in some embodiments in the range of 50 µm to 100 µm. Other diameters are possible as well. The wire of the first helically-wound wire 502 and the wire of the second helically-wound wire 504 may have the same or differing diameters.

While the first helically-wound wire 502 and the second helically-wound wire 504 are shown to be substantially the same length, in one example the first helically-wound wire 502 may be longer or shorter than the second helically-wound wire 504. In another example, the first helically-wound wire 502 and the second helically-wound wire 504 may be staggered such that the first helically-wound wire 502 extends beyond the second helically-wound wire 504 in one direction and the second helically-wound wire extends beyond the first helically-wound wire 502 in the other direction. Other examples are possible as well.

As shown, the first helically-wound wire 502 includes a plurality of turns at an angle relative to the length of the lead 500. The angle may be between, for example, about 0° and 90° in either direction, relative to the length of the lead. Other examples are possible as well. Additionally, as shown, the second helically-wound wire 504 includes a plurality of turns at an angle relative to the length of the lead 500. The angle may be between, for example, about 0° and 90° in either direction, relative to the length of the lead. In one example, such as that shown in FIG. 5*a*, the turns of the second helically-wound wire 504 may be at an angle in a direction opposite an angle of the first plurality of turns, such that the first helically-wound wire 502 and the second helically-wound wire 504 form a sort of cross-hatch. Alternately or additionally, the turns of the first helically-wound wire 502 may be clockwise, while the turns of the second helically-wound wire 504 are counterclockwise (or vice versa), such that the first helically-wound wire 502 and the second helically-wound wire 504 form a sort of cross-hatch. The cross-hatches thus formed may, in some cases, provide improved resistance to penetration or pressure (e.g., by surgical tools). Further, the cross-hatches may, in some cases, be malleable so as to minimize an overall stiffness of the lead 500. The improved resistance to pressure as well as the malleability exhibited by the cross-hatched helically-wound wires 502, 504 may be desirable in certain applications. Other examples are possible as well.

The cross-sectional view shown in FIG. 5B is a cross-section of the lead 500 cut along the line 5B-5B from FIG. 5A. As shown, the lead 500 includes at least one conductive pathway 506 surrounded by a material 508. Each of the conductive pathway 506 and the material 508 may take any of the forms described above in connection with FIGS. 3A-B.

As shown, the first and second helically-wound wires 502, 504 surround the lead 500. In some embodiments, however, the first and second helically-wound wires 502, 504 may be encased within the lead 500. For example, the material 508 may surround each of the first helically-wound wire 502 and the second helically-wound wire 504. As another example, the material 508 may surround the first helically-wound wire 502 and the second helically-wound wire 504 may surround the material 508. As yet another example, an additional layer of material, such as silicone rubber, polyurethane or the like, may surround all or a portion of the first helically-wound wire 502 and/or the second helically-wound wire 504. Other configurations are possible as well, including those involving additional conductive pathways 506 and/or materials 508.

As noted above, a stiffness of the protective element may be varied along a length of the lead 500. In embodiments where the protective element includes a first helically-wound wire 502 and a second helically-wound wire 504, the varied stiffness may be achieved by varying one or both of a pitch of the first helically-wound wire 502 along the length of the first helically-wound wire 502 and a pitch of the second helically-wound wire 504 along the length of the second helically-wound wire 504.

In one example, a pitch of the first helically-wound wire 502 may vary along a length of the first helically-wound wire 502, while a pitch of the second helically-wound wire 504 remains constant. In another example, a pitch of the second helically-wound wire 504 may vary while a pitch of the first helically-wound wire 502 remains constant, or a pitch of both the first helically-wound wire 502 and the second helically-wound wire 504 may vary along their respective lengths. In yet another example, a pitch of the first helically-wound wire 502 may vary in some portions and be constant in other portions along the length of the lead 500, and a pitch of the second helically-wound wire 504 may vary in some portions and be constant in other portions along the length of the lead 500. The first helically-wound wire 502 may vary in some or all of the same portions as the second helically-wound wire 504. Other examples are possible as well.

In the embodiment shown in FIG. 5B, a pitch of the first helically-wound wire 502 is varied along a length of the first helically-wound wire 502, while a pitch of the second helically-wound wire 504 remains constant along its length. In particular, as shown, the first helically-wound wire 504 has a first pitch 510 at a first location along the first helically-wound wire 504 and a second pitch 512 at second location along the first helically-wound wire 504. As a result of the variation between the first pitch 510 to the second pitch 512, a stiffness of the lead 500 may vary from one end of the first helically-wound wire 504 to the other. In particular, as shown, because the first pitch 510 is smaller than the second pitch 512, the first helically-wound wire 502 may be stiffer near the first pitch 510 than near the second pitch 512.

While only two pitches are labeled, it is to be understood that the pitch of the first helically-wound wire 502 may vary along the entire length of the helically-wound wire 502. Similarly, the pitch of the second helically-wound wire 504 may vary along the entire length of the second helically-wound wire 502. For either helically-wound wire, the pitch may be varied such that a stiffness of the lead 500 increases from one end of the helically-wound wire to the other. In another example, the pitch may be varied such that a stiffness of the lead 500 decreases from one end of the helically-wound wire to the other. In particular, the pitch may be varied such that a stiffness of the lead 500 is highest near the connector and decreases along the lead 500 towards the internal component. In still another example, the pitch may be varied such that a stiffness of the lead 500 is greatest towards the middle or other point along the length of the helically-wound wire and decreases towards the ends of the helically-wound wire. In yet another example, the pitch may be varied such that a stiffness of the lead 500 both increases and decreases one or more times from one end of the helically-wound wire to the other. In still another example, the pitch may be varied along some portions of the helically-wound wire and may remain constant along other portions. Other examples are possible as well.

In embodiments where both a pitch of the first helically-wound wire 502 and a pitch of the second helically-wound wire 504 vary, the pitches may vary in the same or different ways. That is, along a given direction, both pitches may increase, both pitches may decrease, or one pitch may increase while the other decreases. Further, the pitch of the first helically-wound wire 502 may, at any point along the lead 500, be greater than, less than, or equal to the pitch of the second helically-wound wire 504. Other variations of the pitches are possible as well.

d. Perforated Tube Protective Element

Figure 6:
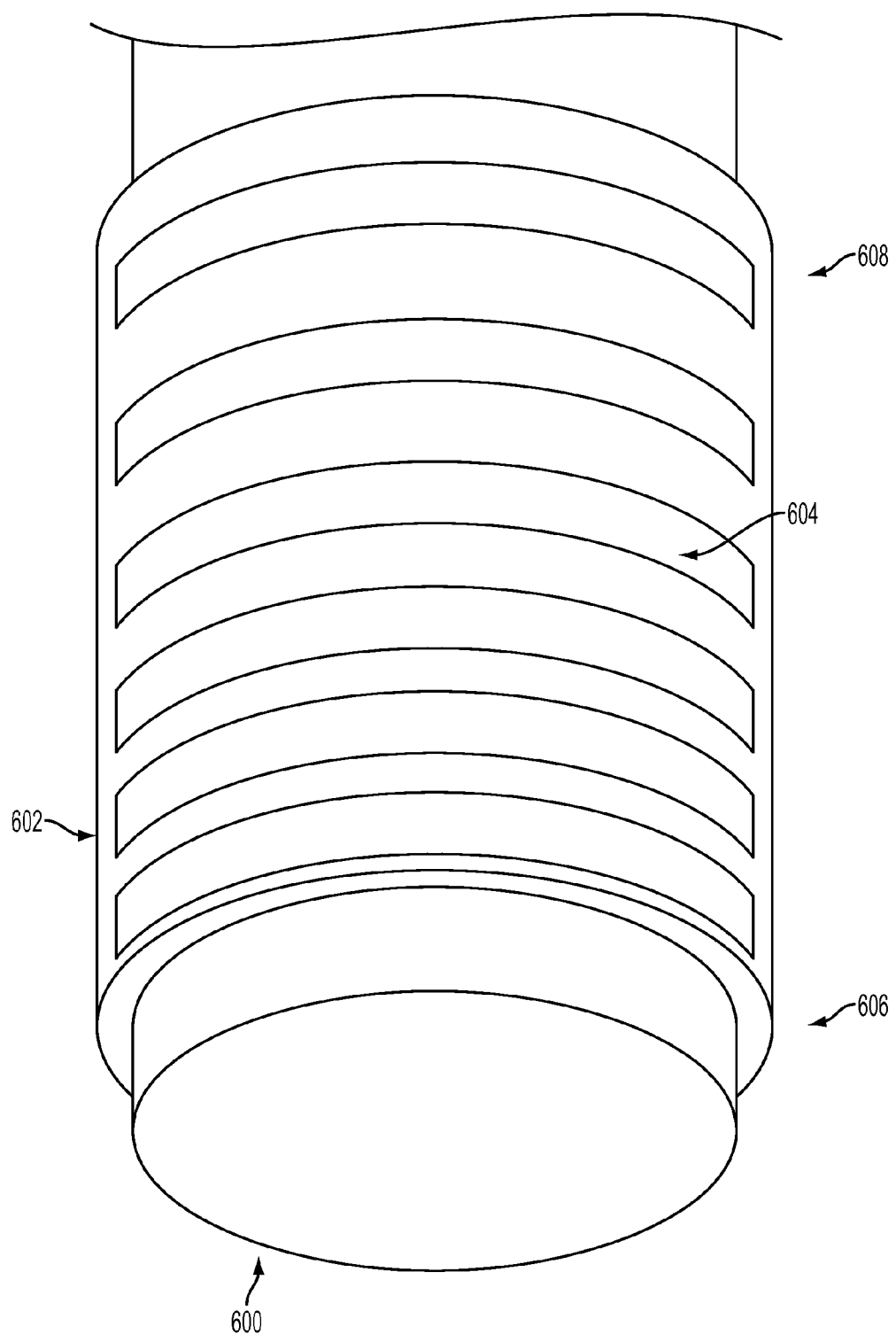
FIG. 6 shows an overview of an example lead including a protective element comprising a perforated tube, in accordance with an embodiment.

FIG. 6 shows an overview of an example lead 600 including a protective element comprising a perforated tube 602, in accordance with an embodiment. The perforated tube 602 may be formed of a number of materials and material compositions including, for example, a metal, a metal alloy, or a polymer. In one example, the perforated tube 602 may comprise a bio-compatible material. Other examples are possible as well.

As shown, the perforated tube 602 includes a plurality of openings 604 cut in the perforated tube 602. The openings 604 may be formed using a laser and/or one or more other cutting techniques including physical, chemical, or other optical cutting techniques. Alternately, the openings 604 may be formed at the same time as the perforated tube 602 using, for example, injection molding, stamping, or another technique. Other examples are possible as well.

The perforated tube 602 may have a variety of thicknesses and inner diameters. In one example, the inner diameter of the perforated tube 602 may be such that the perforated tube 602 fits snugly around the lead 600. In another example, the thickness of the perforated tube 602 may be tapered at the edges of the perforated tube 602 to provide a smooth boundary between the perforated tube 602 and the surface of the lead 600. Other examples are possible as well.

As noted above, a stiffness of the protective element (in this embodiment the perforated tube 602) may be varied along a length of the protective element. In the embodiment shown in FIG. 6, the varied stiffness of the perforated tube 602 is achieved by varying a ratio of openings to tube in the perforated tube 602 along the length of the perforated tube 602. For example, a larger number of openings 604 may be made in one portion of the perforated tube 602 than in another. As another example, openings 604 having a larger area may be made in one portion of the perforated tube 602 and openings 604 having a smaller area may be made in another portion of the perforated tube 602. In another embodiment, the varied stiffness of the perforated tube 602 may be achieved by varying how far the openings 604 extend circumferentially around the perforated tube 602. For example, some openings 604 may extend further around the perforated tube 602, resulting in a decreased stiffness as compared to openings 604 that do not extend as far around the perforated tube 602. Other examples are possible as well. In some embodiments, such as that shown in FIG. 6, the openings 604 may extend in a direction substantially perpendicular to a length of the lead. In other embodiments, the openings 604 may extend in a direction that is at an angle to the length of the lead, such that the openings 604 form a sort of helix around the perforated tube 602. Other configurations are possible as well.

As shown, the openings 604 are closer together on one end 606 of the perforated tube 602 and further apart on the other end 608, such that there is a higher ratio of openings to tube on the one end 606 of the perforated tube 602 as compared with the other end 608. As a result, the end 608 of the perforated tube 602 having a lower ratio of openings to tube may be stiffer than the other end 606. The ratio of openings to tube in the perforated tube 602 may vary along the length of the perforated tube 602 in a number of ways. In one example, the ratio of openings to tube may be varied such that a stiffness of the perforated tube 602 increases or decreases from one end of the perforated tube 602 to the other. In particular, the ratio of openings to tube may be varied such that a stiffness of the lead 600 is highest near the connector and decreases along the lead 600 towards the internal component. In another example, the ratio of openings to tube may be varied such that a stiffness of the perforated tube 602 is greatest towards the middle or other point along the length of the perforated tube 602 and decreases towards the ends of the perforated tube 602. In yet another example, the ratio of openings to tube may be varied such that a stiffness of the perforated tube 602 both increases and decreases one or more times from one end of the perforated tube 602 to the other. In still another example, the ratio of openings to tube may be varied along some portions of the perforated tube 602 and may remain constant along other portions of the perforated tube 602. Other examples are possible as well.

While not shown, the lead 600 will typically include one or more conductive pathways and layers of material, as shown in the previous embodiments. Each of the conductive pathways and materials may take any of the forms described above in connection with FIGS. 3A-B.

As shown, the perforated tube 602 surrounds the lead 600 such that the perforated tube 602 is located on an exterior surface of the lead 600. In other embodiments, the perforated tube 602 may be encased within the lead 600. For example, a layer of material, such as silicone rubber, polyurethane or the like, may surround all or a portion of the perforated tube 602. Other examples are possible as well.

e. Patterned Mesh Protective Element

Figure 7A:
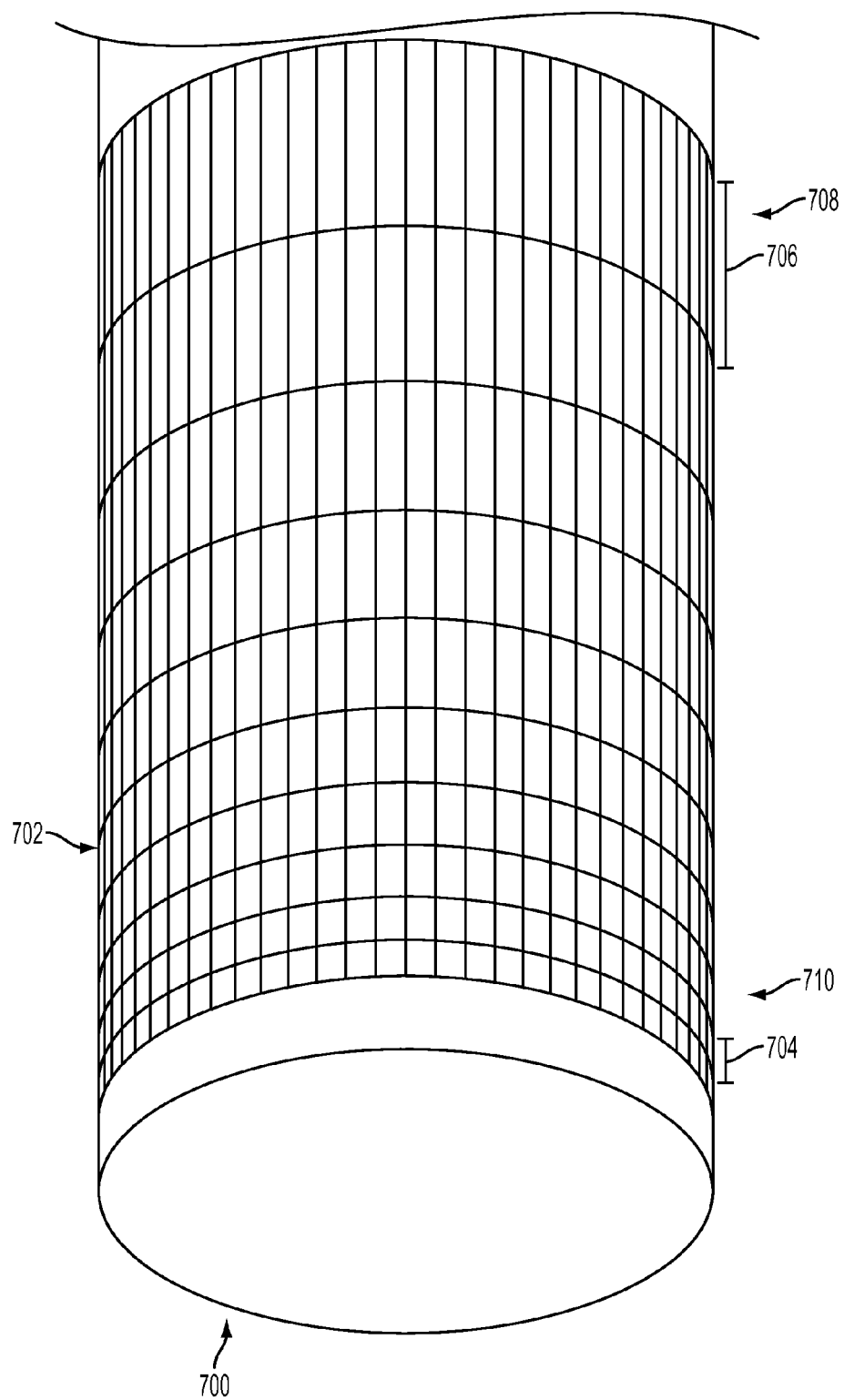
FIGS. 7A-B show overviews of example leads including a protective element comprising a patterned mesh, in accordance with an embodiment.
Figure 7B:
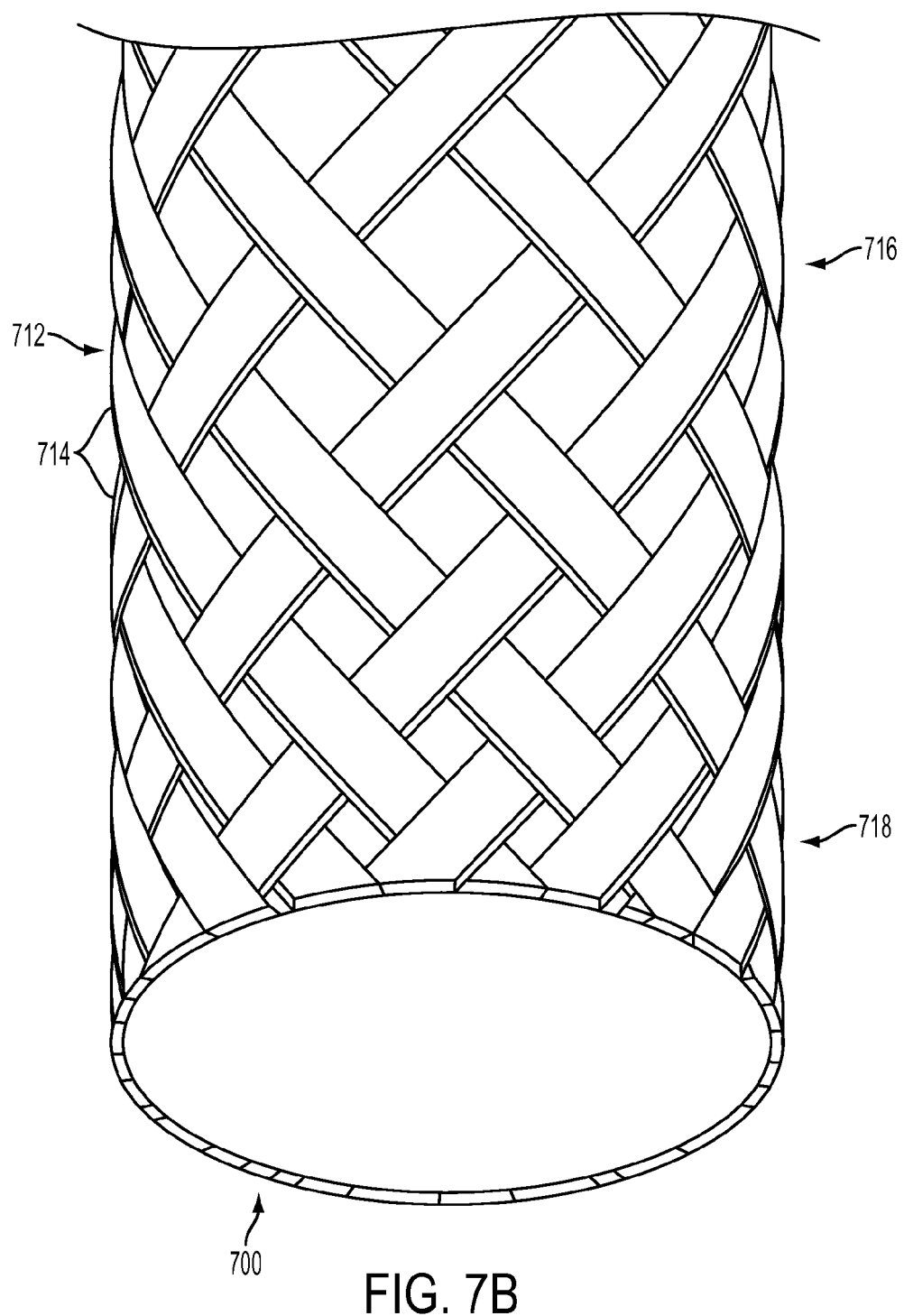

FIGS. 7A-B show overviews of an example lead 700 including a protective element comprising a patterned mesh, in accordance with an embodiment.

A first patterned mesh 702 is shown in FIG. 7A. The patterned mesh 702 may be formed of one or more materials and/or material compositions including, for example, a metal, a metal alloy, or a polymer. In one example, the patterned mesh 702 may comprise a bio-compatible material. Other examples are possible as well.

The patterned mesh 702 may take several forms. In one example, the patterned mesh 702 may be a tube-like mesh that surrounds the lead 700. To this end, the patterned mesh 702 may have a variety of thicknesses and inner diameters. For instance, the inner diameter of the patterned mesh 702 may be such that the patterned mesh 702 fits snugly around the lead 700. Further, for instance, the thickness of the patterned mesh 702 may be tapered at the edges of the patterned mesh 702 to provide a smooth boundary between the patterned mesh 702 and the surface of the lead 700. In another example, the patterned mesh 702 may be patterned directly onto the lead 700 using, for example, a sputtering process. To this end, the thickness of the patterned mesh 702 may be very thin and/or may be tapered at the edges of the patterned mesh 702 to provide a smooth boundary between the patterned mesh 702 and the surface of the lead 700. Other examples are possible as well.

As noted above, a stiffness of the protective element (in this embodiment the patterned mesh 702) may be varied along a length of the protective element. In the embodiment shown in FIG. 7A, the varied stiffness of the patterned mesh 702 is achieved by varying a pattern of the patterned mesh 702 along the length of the patterned mesh 702. As shown, the elements of the pattern on one end 708 of the patterned mesh 702 be spaced a larger distance 706 apart, while the elements on the other end 710 of the patterned mesh 702 may be spaced a smaller distance 704 apart. As a result, the end 710 of the patterned mesh 702 having more closely spaced elements may be stiffer than the other end 708. In some embodiments, rather than varying a spacing of elements in a pattern along the patterned mesh 702, the elements of the pattern themselves may vary along the length of the patterned mesh 702. For example, in the patterned mesh 702 shown in FIG. 7A, the elements of the pattern are rectangles. In some embodiments, in order to vary the stiffness of the patterned mesh 702, the elements of the pattern may vary from being rectangles to being, for example circles along the length of the patterned mesh 702. Other examples are possible as well.

A second patterned mesh 712 is shown in FIG. 7B. As shown, the patterned mesh 712 may be a tube-like mesh formed by braiding together a number of threads 714. The threads 714 of the patterned mesh 712 may be formed of one or more materials and/or material compositions including, for example, a metal, a metal alloy, or a polymer. The threads 714 may be formed of the same material or of differing materials. In one example, one or more of the threads 714 may comprise a bio-compatible material. Other examples are possible as well.

As noted above, a stiffness of the protective element (in this embodiment the patterned mesh 712) may be varied along a length of the protective element. In the embodiment shown in FIG. 7B, the varied stiffness of the patterned mesh 712 is achieved by varying how tightly or loosely the patterned mesh 712 is braided. As shown, the patterned mesh 712 is more loosely knit on one end 716 than on the other end 718. In other embodiments, the varied stiffness of the patterned mesh 712 may be achieved by varying, for example, the material or material composition of one or more of the threads 714, and/or a ratio of the threads 714 to one another along the length of patterned mesh 712. Other examples are possible as well.

In other embodiments, a tube-like patterned mesh formed by knitting together a number of threads may be used. The threads of the patterned mesh may be formed of any of the materials described above, and may be formed of the same material or of differing materials. As noted above, a stiffness of the protective element (in this embodiment the knitted patterned mesh) may be varied along a length of the protective element, such as by varying how tightly or loosely the patterned mesh is knitted and/or by varying the material or material composition of one or more of the threads, and/or a ratio of the threads to one another along the length of knitted patterned mesh. Other examples are possible as well.

In any of the patterned meshes described above, the stiffness of the patterned mesh may vary along the length of the patterned mesh in a number of ways. In one example, the stiffness of the patterned mesh may increase or decrease from one end of the patterned mesh to the other. In particular, the stiffness of the patterned mesh may be highest near the connector and may decrease along the lead 700 towards the internal component. In another example, the stiffness of the patterned mesh may be greatest towards the middle or another point along the length of the patterned mesh and may decrease towards the edges of the patterned mesh. In yet another example, the stiffness of the patterned mesh may both increase and decrease one or more times from one end of the patterned mesh to the other. In still another example, the stiffness may be varied along some portions of the patterned mesh and may remain constant along other portions of the patterned mesh. Other examples are possible as well.

While not shown, the lead 700 may additionally include one or more conductive pathways and layers of material, as shown in the previous embodiments. Each of the conductive pathways and the materials may take any of the forms described above in connection with FIGS. 3A-B.

As shown, each of the patterned meshes 702, 710 surrounds the lead 700 such that the patterned mesh is located on an exterior surface of the lead 700. In other embodiments, the patterned mesh may be encased within the lead 700. For example, a layer of material, such as silicone rubber, polyurethane or the like, may surround all or a portion of the patterned mesh. Other examples are possible as well.

3. Conclusion

It is to be understood that the configurations shown in the figures are merely illustrative and are not intended to be limiting. In particular, the sizes, shapes, and positions of the elements shown in the figures are merely illustrative, and other sizes, shapes and positions are possible as well. Further, the various features of the configurations shown in the figures may be added, removed, combined, or otherwise modified to result in many more configurations that are similarly contemplated.

While the foregoing description focused on cochlear implants, it is to be understood that implantable lead disclosed herein could be used in any number of other implantable devices including but not limited to auditory brainstem implant systems, deep brain stimulation systems, and midbrain stimulation systems. Other types of implantable devices are possible as well.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An implantable lead comprising:
at least one conductive pathway; and
a protective element surrounding at least a portion of the at least one conductive pathway, wherein a stiffness of the protective element varies along a length of the protective element, and wherein the protective element is selected from the group consisting of a single helically-wound wire, two helically-wound wires, a perforated tube, and a patterned mesh.

2. The implantable lead of claim 1, wherein the protective element comprises a first helically-wound wire.

3. The implantable lead of claim 2, wherein the stiffness varying along the length of the protective element comprises a pitch of the first helically-wound wire varying along a length of the first helically-wound wire.

4. The implantable lead of claim 2, wherein the first helically-wound wire comprises a plurality of turns, each turn being at an angle between about 15° and 75° relative to a length of the implantable lead.

5. The implantable lead of claim 2, wherein the protective element further comprises a second helically-wound wire.

6. The implantable lead of claim 5, wherein the second helically-wound wire at least partially overlays the first helically-wound wire.

7. The implantable lead of claim 5, wherein the first helically-wound wire comprises a first plurality of turns, and wherein the second helically-wound wire comprises a second plurality of turns, each turn of the second plurality of turns being at an angle between about 15° and 75° relative to a length of the implantable lead and substantially non-parallel to the first plurality of turns.

8. The implantable lead of claim 5, wherein the stiffness varying along the length of the protective element comprises a pitch of the second helically-wound wire varying along a length of the second helically-wound wire.

9. The implantable lead of claim 1, wherein the protective element comprises a perforated tube.

10. The implantable lead of claim 9, wherein the stiffness varying along the length of the protective element comprises a ratio of cuts to tube in the perforated tube varying along a length of the perforated tube.

11. The implantable lead of claim 1, wherein the protective element comprises a patterned mesh.

12. The implantable lead of claim 11, wherein the stiffness varying along the length of the protective element comprises a pattern of the patterned mesh varying along a length of the patterned mesh.

13. The implantable lead of claim 1, wherein the stiffness varying along the length of the protective element comprises the stiffness reducing along the length of the protective element.

14. An implantable device, comprising:
a lead comprising a connector, at least one conductive pathway, and a protective element surrounding at least a portion of the at least one conductive pathway,
wherein a stiffness of the protective element varies along a length of the protective element, and wherein the protective element is selected from the group consisting of a single helically-wound wire, two helically-wound wires, a perforated tube, and a patterned mesh.

15. The implantable device of claim 14, wherein the protective element extends from the connector along a length of the lead.

16. The implantable device of claim 15, wherein the stiffness of the protective element varying along the length of the protective element comprises the stiffness being greatest at the connector and reducing along the length of the lead away from the connector.

17. The implantable device of claim 14, wherein the protective element comprises a first helically-wound wire and a second helically-wound wire at least partially overlaying the first helically-wound wire.

18. The implantable device of claim 17, wherein the first helically-wound wire comprises a first plurality of turns, each turn of the first plurality of turns being at an angle between about 15° and 75° relative to a length of the lead, and wherein the second helically-wound wire comprises a second plurality of turns, each turn of the second plurality of turns being at an angle between about 15° and 75° relative to the length of the lead and substantially non-parallel to the first plurality of turns.

19. The implantable device of claim 17, wherein the stiffness of the protective element varying along a length of the protective element comprises at least one of varying a pitch of the first helically-wound wire along a length of the first helically-wound wire and varying a pitch of the second helically-wound wire along a length of the second helically-wound wire.

20. The implantable device of claim 14, wherein the connector is configured to be connectable to a separate module.

21. A cochlear implant, comprising:
a stimulator configured to generate a stimulation current;
a lead configured to conduct the stimulation current between the stimulator and at least one stimulation site, the lead comprising
at least one conductive pathway and
a protective element surrounding at least a portion of the at least one conductive pathway, wherein a stiffness of the protective element varies along a length of the protective element.

22. The cochlear implant of claim 21, wherein the protective element extends along a length of the lead.

23. The cochlear implant of claim 22, wherein the stiffness of the protective element varying along a length of the protective element comprises the stiffness reducing along the length of the lead.

24. The cochlear implant of claim 21, wherein the protective element comprises a first helically-wound wire and a second helically-wound wire surrounding the first helically-wound wire.

25. The cochlear implant of claim 24, wherein the first helically-wound wire comprises a plurality of turns, each turn being at an angle between about 15° and 75° relative to a length of the lead, and wherein the second helically-wound wire comprises a second plurality of turns, each turn being at an angle between about 15° and 75° relative to the length of the lead and substantially non-parallel to the first plurality of turns.

26. The cochlear implant of claim 24, wherein the stiffness of the protective element varying along a length of the protective element comprises at least one of varying a pitch of the first helically-wound wire along a length of the first helically-wound wire and varying a pitch of the second helically-wound wire along a length of the second helically-wound wire.

27. The cochlear implant of claim 21, further comprising a second lead configured to connect the stimulator to a separate module, the second lead comprising a connector for connecting to the separate module, a second conductive pathway, and a second protective element surrounding at least a portion of the second conductive pathway, wherein a stiffness of the second protective element varies along a length of the second protective element.

* * * * *